United States Patent [19]

McKenna

[11] Patent Number: 5,473,657

[45] Date of Patent: Dec. 5, 1995

[54] X-RAY TOMOGRAPHIC SCANNING SYSTEM

[75] Inventor: Gilbert W. McKenna, Revere, Mass.

[73] Assignee: Analogic Corporation, Peabody, Mass.

[21] Appl. No.: 359,845

[22] Filed: Dec. 20, 1994

Related U.S. Application Data

[63] Continuation of Ser. No. 193,783, Feb. 8, 1994, abandoned.

[51] Int. Cl.$^6$ ......................................................... A61B 6/04
[52] U.S. Cl. ................................................ 378/4; 378/15
[58] Field of Search ................................. 378/4, 15, 17, 378/146, 193, 196, 197

[56] References Cited

U.S. PATENT DOCUMENTS

| | | | |
|---|---|---|---|
| 4,201,430 | 5/1980 | Dinwiddle et al. | 250/445 |
| 4,928,283 | 5/1990 | Gordon | 378/20 |
| 5,093,850 | 3/1992 | Dinwiddie et al. | 378/15 |
| 5,109,397 | 4/1992 | Gordon et al. | 378/4 |

FOREIGN PATENT DOCUMENTS

| | | |
|---|---|---|
| 80400488.5 | 12/1980 | France . |
| 8429531.7 | 5/1986 | Germany . |
| 8703190.6 | 8/1988 | Germany . |

*Primary Examiner*—David P. Porta
*Assistant Examiner*—Don Wong
*Attorney, Agent, or Firm*—Lappin & Kusmer

[57] ABSTRACT

An improved X-ray tomography system having an X-ray source, X-ray detector assembly and support means including a frame supporting a rotatable drum on which at least the source is mounted for rotation in a scanning plane about an axis of rotation. The rotatable drum is supported for centerless rotation on a cradle formed by resilient rollers, with the top half of the drum free to expand or contract as a result of temperature changes. The rollers are resilient so as to dampen vibration transfer between the frame and drum.

9 Claims, 3 Drawing Sheets

X-RAY TOMOGRAPHIC SCANNING SYSTEM

This is a continuation of application Ser. No. 08/193,783 filed on Feb. 8, 1994, abandoned.

RELATED APPLICATIONS

This application is related to U.S. patent application Ser. No. 08/193,696, filed in the names of Ronald E. Swain and Gilbert W. McKenna and entitled "Tomographic Scanner Having Center of Rotation for all Physics" (Attorney's Docket No. ANA-31); U.S. patent application Ser. No. 08/193,562, filed in the name of Gilbert W. McKenna and entitled "X-ray Tomography System with Gantry Pivot and Translation Control" (Attorney's Docket No. ANA-37); and U.S. patent application Ser. No. 08/193,782, filed in the name of Gilbert W. McKenna and entitled "Stabilized, Cantilevered Patient Trauma Table System" (Attorney's Docket No. ANA-58); all filed simultaneously herewith and assigned to the present assignee.

FIELD OF THE INVENTION

The present invention relates generally to X-ray tomographic scan apparatus, and more particularly to computerized axial tomography (CAT) scan systems.

BACKGROUND OF THE INVENTION

Current CAT scan systems usually include a gantry formed of a structure such as a centrally apertured disk or drum rotatable within a frame, and at least an X-ray source mounted on the drum for rotational motion about a table on which a patient can repose. The X-ray source may provide periodic pulses or continuous wave radiation. In third generation CAT scan systems the X-ray detector system is in the form of a detector array secured to the drum, diametrically opposite the source. In fourth generation CAT scan systems the X-ray detectors are disposed around the frame and are positioned to detect X-rays as the drum rotates about its axis. Each detector typically is either solid state or a gas tube. The detector system is aligned with the source so that the detector system and source are positioned within a common mean, scanning or rotation plane (usually perpendicular to the axis of rotation of the drum). In the case of a detector array found on third generation systems, each detector of the detector array is positioned in the scanning plane at a predetermined angular spacing relative to the source so that each detector subtends an equal angle relative to the focal spot of the X-ray tube, thus providing a plurality of different X-ray paths in the scanning plane between the source and the respective detectors. In fourth generation machines the stationary detectors each define a focal point for the X-ray paths from various positions of the source, as the latter rotates about the rotation axis. In both types of systems the X-ray paths can collectively resemble a fan, and consequently such systems are sometimes referred to as "fan beam" tomography systems.

These tomography systems each provides a plurality of information or data signals representing variations in the radiation flux measured by the respective detectors at predetermined angular positions of the drum during rotation of the drum about an object positioned in the space between the detectors and the X-ray source. Processing these data signals in accordance with known (Radon) mathematical relationships, a visual image can be formed, or "reconstructed," representing a two-dimensional slice along the plane of rotation, i.e., the scanning plane, through the portion of the scanned object positioned in the plane. The formation of such "reconstructed" images critically depends upon the components mounted on the rotating drum rotating precisely about the axis of rotation so that no lateral movement occurs between the moving drum relative to the object being scanned.

Because even minor mechanical noise and/or artifacts causing undesirable lateral motion of the elements of the CAT scan apparatus during a scan relative to the object, particularly those occurring within the scanning plane normal to the axis of rotation, can cause errors resulting in faulty or erroneous image information, such apparatus typically has been provided as massively reinforced machines often weighing a ton or more in order to reduce motion due to such mechanical noise and artifacts. Consequently, because of the weight, the massive drum has usually been supported in the frame by an expensive and heavy precision roller bearing or ball bearing assembly.

Many of the disadvantages inherent in such a massive, expensive, relatively fixed CAT scan structure characteristic of the prior art have been recognized and addressed, at least in part, by the apparatus described and claimed in U.S. Pat. No. 4,928,283 issued May 22, 1990 to B. M. Gordon, and in U.S. Pat. No. 5,109,397 issued Apr. 28, 1992 to B. M. Gordon, et al., both assigned to the present assignee. In the aforesaid '283 patent, the patentee broadly suggests the use of wheels rather than bearings for rotatably supporting the drum in a frame, without however any discussion of the nature and characteristics of such wheels. The simple replacement of bearings with wheels may introduce deviations or wobble as the drum is rotated in its plane, resulting in undesirable inaccuracies in the tomographic image produced. The '397 patent addresses, inter alia, the use of electromechanical sensors that follow the outer periphery of the disc in the plane of rotation to provide compensating electrical signals for modifying or correcting the data received by the X-ray detection array.

In addition, the massive drum of the prior art system can be subjected to changes in temperature from heat generated by the X-ray source. To the extent this heat is transferred to the drum, the drum will expand in accordance with its coefficient of thermal expansion, and only contract when the source is allowed to cool. Since the drum is sized to rotate within the bearing race at ambient temperature, as the drum expands compressive forces are created on the bearings resulting in stress related failures. Accordingly, heat transfer devices and the like are frequently used so as to minimize the effects of heat on the components from the use of the X-ray source. However, heat sinks merely add additional weight and therefore stress to the bearings. As a result, the bearings and races have to be replaced from time to time. But because of the weight of the drum, this problem can be difficult to service and time consuming. While wheels are suggested in the '283 patent as a replacement for the bearings, the patent is silent as to the problem associated with heat expansion or how wheels overcome the problem.

OBJECTS AND SUMMARY OF THE INVENTION

Accordingly, it is a primary object of the present invention to provide an improved X-ray tomographic scan system that overcomes the problems inherent in the massive, heavy and poorly mobile prior art systems.

Another object of the present invention is to provide such an improved scan system that includes a gantry in which the drum is supported for "centerless" rotation within the frame by rollers, while maintaining or improving the precision at which the system accurately scans during drum rotation regardless of thermal expansion.

Yet another object of the present invention is to provide such an improved scan system in which the drum is supported by a system of compliant, error averaging, roller trucks.

Other objects of the present invention are to provide such a system that includes a drum that is of a relatively smaller mass and rotatably mounted to the frame of the gantry so as to easily accommodate temperature cycling from the use of the X-ray source; and to provide such a system that reduces to a substantial extent the power required to rotate the drum.

The objects of the present invention are effected generally by the provision of an improved X-ray tomography structure comprising an X-ray source, X-ray detection means preferably including a plurality of detectors, and support means including a frame supporting a rotatable assembly, preferably including a gantry drum. At least the X-ray source is mounted on the rotatable assembly for centerless rotation in a scanning plane about an axis of rotation such that X-rays from the source projected in the scanning plane through a plurality of angular positions may pass through an object and be detected by at least one or more of the detectors. In one embodiment of the invention, the drum is mounted on a cradle of a plurality of compliant rollers made of a resilient material. The resilient rollers serve to (a) dampen the transfer of vibrations to the drum as the latter rotates and (b) accommodate temperature cycling of the drum. In the preferred embodiment the entire mass of the drum rests upon at least two pairs (and preferably four pairs) of rollers so that the top half of the drum is unconstrained (for centerless rotation) so as to allow the drum to freely expand and contract without introducing error-producing stresses into the drum or frame. Each pair of rollers (and preferably two pairs of rollers) is mounted in an elastically compliant truck, the truck being pivotably supported about a pivot axis disposed between and parallel to the rotational axes of the two rollers supported by the truck.

Other objects of the present invention will in part be obvious and will in part appear hereinafter. The invention accordingly comprises the apparatus possessing the construction, combination of elements and arrangement of parts exemplified in the following detailed disclosure and the scope of the application of which will be indicated in the claims.

BRIEF DESCRIPTION OF THE DRAWINGS

For a fuller understanding of the nature and objects of the present invention, reference should be had to the following detailed description taken in connection with the accompanying drawings wherein.

DETAILED DESCRIPTION OF THE DRAWINGS

Figure 1:
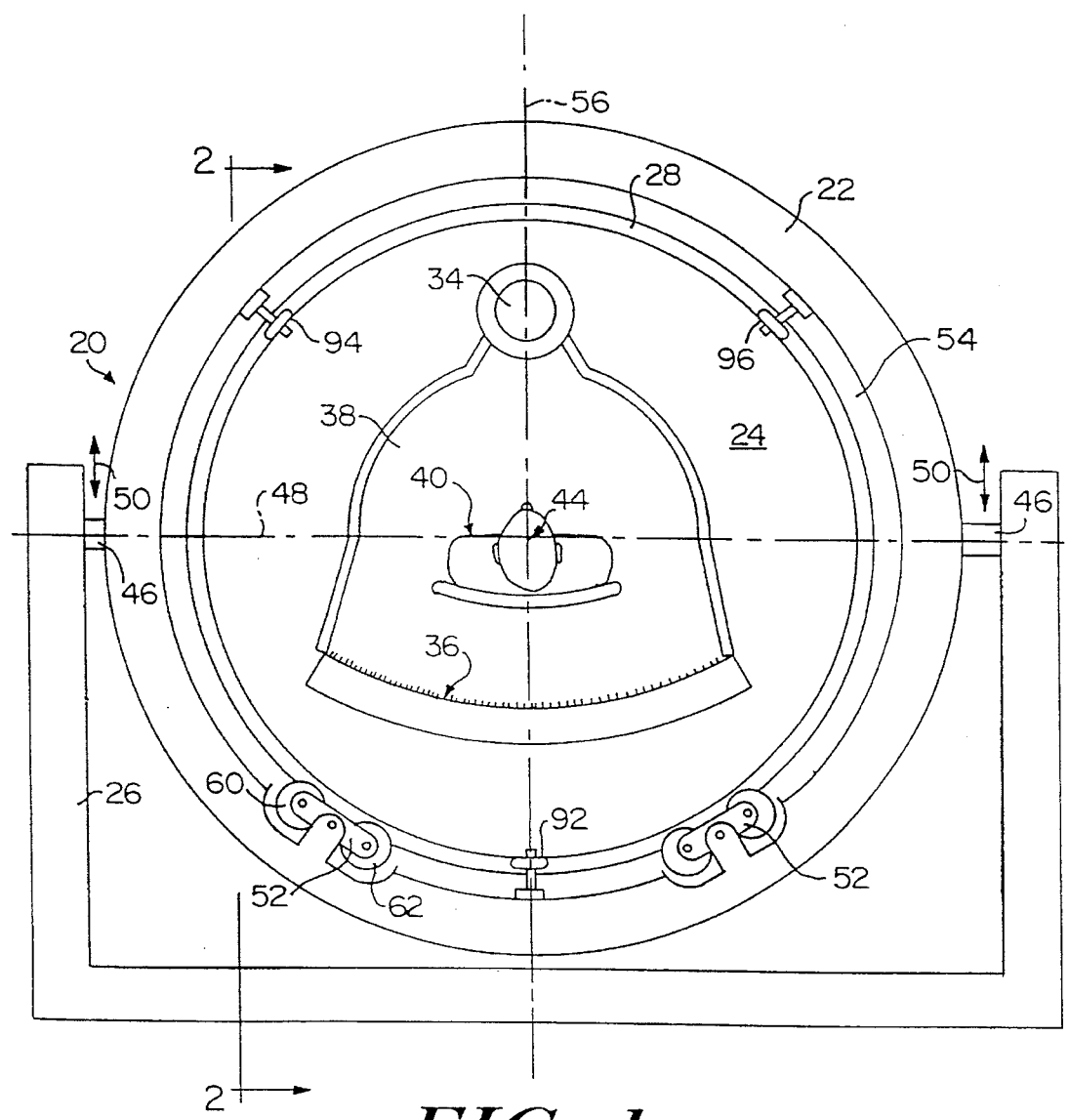
FIG. 1 is a schematic plan view of structure illustrating an X-ray tomographic scan gantry of the third generation type constructed according to the principles of the present invention.
Figure 2:
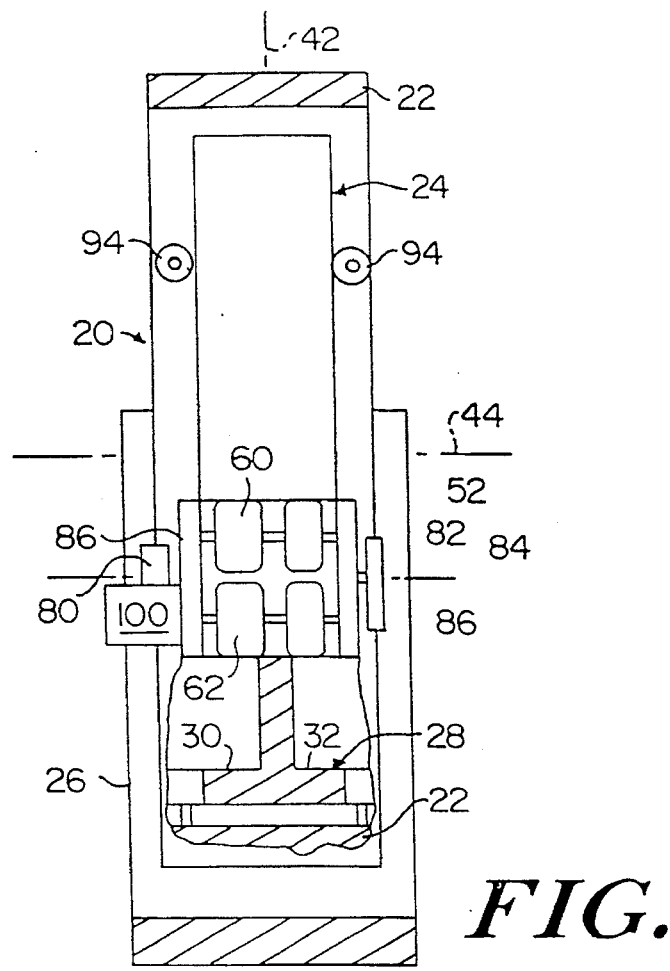
FIG. 2 is an enlarged side view, partly broken-away, taken along the line 2—2 of FIG. 1.

Referring now to FIGS. 1 and 2, there is shown a gantry 20 of a tomography system of the third generation type embodying the principles of the present invention, and typically formed of supporting frame 22 and drum 24; both pivotably supported on a cart 26. The drum may be provided as a circular, substantially planar, hollow ring or annulus typically of about 135 cm. in outer diameter. Drum 24 is preferably, relative to its diameter, quite thin, e.g. about 1.25 cm., although these dimensions can vary. As shown in FIG. 2, drum 24 is typically formed as a hollow ring or annulus having a rectangular cross-section. As seen in FIG. 2 outer peripheral member 28 of the drum is typically a rolled extrusion of light-weight, rigid material such as aluminum, magnesium-aluminum alloy and the like, so as to form a smooth, circular, outer band with transversely projecting edge lips 30 and 32 extending radially outwardly. Stiffening or bracing components (not shown), such as ribs formed in the disk, can be provided if desired, to substantially minimize or preclude motion or flexure of drum 24 transversely to its mean plane.

As shown in FIG. 1, fixedly mounted on drum 24 for rotational motion therewith, are other components of the apparatus, such as X-ray source 34 and detector array 36. The configuration of drum 24 provides central aperture 38 preferably dimensioned so that the body 40 of a patient on a table can be inserted therethrough. Source 34 is positioned to direct a beam of X-rays substantially along the mean plane 42 (see FIG. 2) (defining the scanning or rotation plane) in the plane of drum 24 across aperture 38, the scanning plane being substantially perpendicular to central axis 44 extending through aperture 38. Similarly, detector array 36 is mounted on drum 24 so as to detect X-rays from source 34 after the latter have traversed aperture 38 within the scanning plane.

Frame 22 typically is formed as a annular ring portion made of the same material as drum 24 and concentric with drum 24 about the periphery of the latter. Frame 22 is pivotally mounted on cart 26 with pivot pins 46, preferably for both rotation about pivot axis 48, and for translational movement vertically along the yoke in the direction of arrows 50, in any suitable manner.

Figure 3:
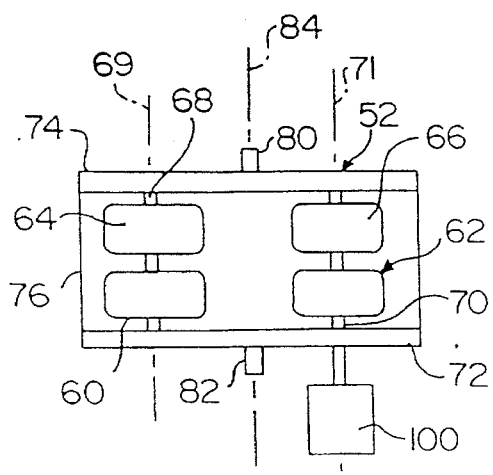
FIG. 3 is an enlarged schematic view of a supporting roller truck and drive mechanism for operating the rotatable assembly of the apparatus of FIG. 1.

As shown in FIGS. 1 and 2, the entire mass of drum 24 is supported by gravity on trucks 52, with the top half of the drum unconstrained in the rotation plane 42 and mounted for centerless rotation about central axis 44 relative to stationary supporting frame 22. Specifically, frame 22 and drum 24 are dimensioned so that the latter is rotatably mounted on roller trucks 52 to provide annular interspace 54, yielding ample clearance between the top half of the outer periphery of drum 24 and the inner periphery of frame 22 so that the disk is free to expand and contract as it heats and cools. In accordance with one embodiment of the present invention, at least two roller trucks 52 are pivotably mounted on frame 22, the trucks being preferably symmetrically disposed at opposite sides of a vertical center line 56 disposed within the plane 42 and extending 14 perpendicularly through axis 44. The trucks are preferably symmetrically positioned between about 15° to 45° about the axis 44 relative to the center line 56. Each roller truck 52 comprises one and preferably at least a pair of tandem rollers 60 and 62 rotatable in a common plane, parallel to or coplanar with the scanning plane. Preferably, as shown in FIGS. 2 and 3, truck 52 is formed of two side-by-side, parallel pairs of such tandem rollers 60 and 62, and 64 and 66. Rollers 60 and 64 are mounted on common axle 68 (defining axis 69) and wheels 62 and 66 mounted on common axle 70 (defining axis 71), axles 68 and 70 (and therefore axes 69 and 71) being parallel with one another and mounted so as to be parallel to rotation axis 44. Each truck includes a parallel side walls 72 and 74 joined by the bottom plate 76. Axles 68 and 70 are respectively mounted adjacent opposite ends of parallel side walls 72 and 74 of the truck. The side walls and bottom plate of the truck are preferably made as an integral piece of elastically compliant material such as plastic, sheet metal and the like. Each of side walls 72 and 74 is pivotably connected intermediate its ends, preferably centrally, through respective coaxial pivots 80 and 82 coupled to respective yoke supports 86 defining a common axis 84. The supports are fixedly mounted to frame 22 so that each truck 52 is pivotable about the common axis 84 of its pivots.

Figure 4:
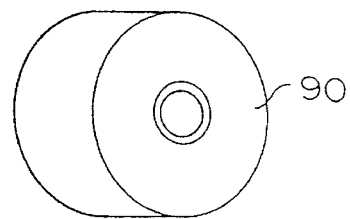
FIG. 4 is a perspective view of a roller used in the roller truck of the embodiment described in connection with FIGS. 1–3.
Figure 5:
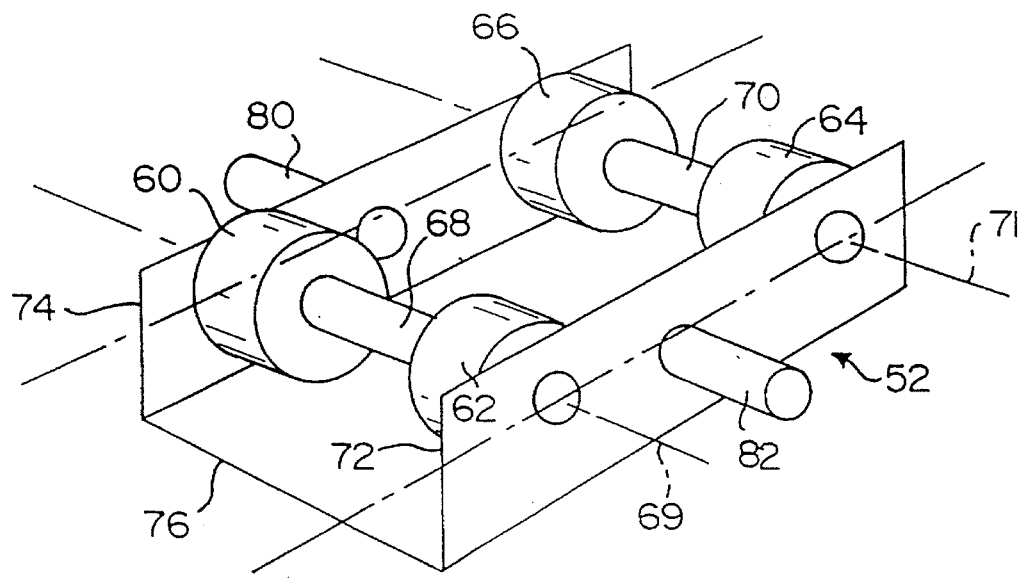
FIG. 5 and 6 illustrate the compliant nature of the roller truck of the FIG. 1 embodiment.

The mounting of roller trucks 52 on the frame 22 insures that most of the bearing noise from rotation of the rollers will be limited to the stationary portion of the gantry. As seen in FIG. 4, each roller preferably includes a pneumatic or other elastic covering or tire 90 intended to contact a peripheral portion of drum 24 and made of a resilient material, such as rubber, nylon, or suitable polymer. Preferably, the tire material is polyurethane in a thickness of about 4 min. and durometer of about 82 (although these values can clearly vary depending upon the design objectives) so as to provide sufficient damping of any mechanical noise and artifacts transmitted from the frame to the drum, and to accommodate thermal expansion of drum 24.

Figure 6:
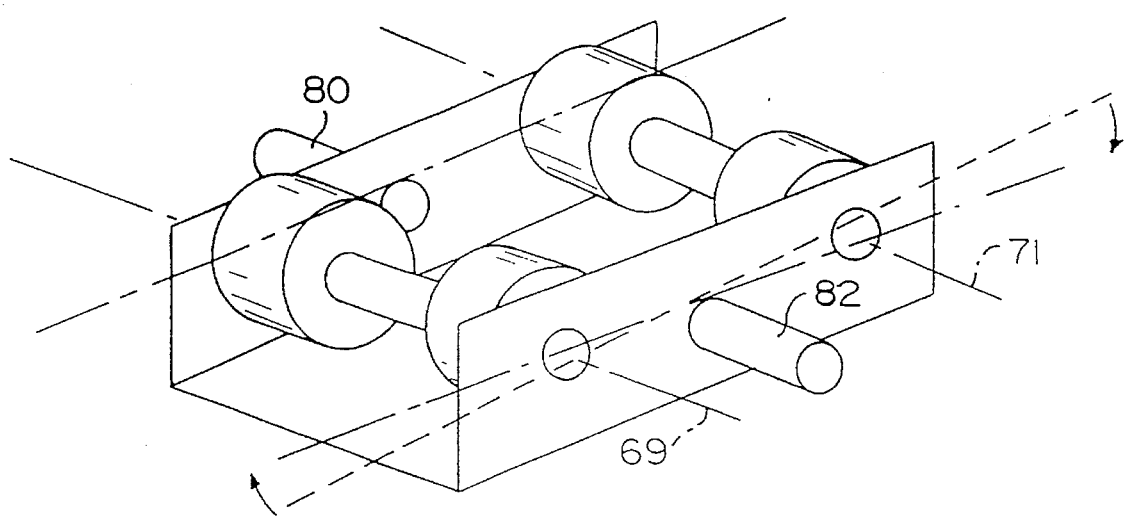

It will be appreciated that tires 90, herein described, are not the equivalent of the roller bearings of the prior art, inasmuch as the operation of roller bearings involve substantial metal-to-metal contact, and generate and transmit substantial amounts of mechanical noise despite the use of lubrication. Further, contact between such roller bearings and the periphery of the drum undesirably generate and transmit such noise and other external vibrations and artifacts directly to the drum. Also, with lighter drum 24 and the supported components (on the order of 1000 pounds), the resilient wheels used to support the drum in accordance with the present invention can also be much lighter in weight than the prior art bearings. The wheels are considerably less expensive and with centerless rotation make servicing and removal of the drum much simpler and easier. Further, any in-place vibration or other force components applied to the drum as the drum rotates about its axis 44, will be transferred to the rollers. Because the structure of each truck is at least in part elastically complacent, lateral movement of the drum within the scanning plan will be reduced since such forces will result in some movement of the rollers about the pivot axis 84 and/or torsional twisting of the axes 69 and 71 relative to one another (as shown in FIG. 6). The torsional twisting is permitted due to the compliant nature of the truck. The compliant nature of the truck permits each roller of a truck to share a like portion of the load and average out any lateral displacement, if any, caused by non-rotational in-plane motions of the drum. With four rollers used per truck, any lateral displacement thus will be approximately one-quarter that which would occur if only a single roller were used. Drum 24 is held within the scanning plane only by gravity on top of the rollers of trucks 52, but any motion of the drum perpendicular to axis 44 is thus minimized or damped by the compliant, elastic mounting provided by tires and by the frame of the trucks.

In addition to trucks 52, as shown in FIGS. 1 and 2, gantry 20 is provided with preferably at least three pairs, of elastic, tire-equipped rollers 92, 94, and 96 (similar to rollers 60, 62, 64, and 66) mounted on frame 22 for rotation along radial lines passing through the axis 44. The pairs of rollers are preferably (although not necessarily) at equiangular increments about the internal periphery of the frame. One tire of the rollers of each pair 92, 94 and 96 is disposed in rolling contact with the corresponding side edge of edge lips 30 of drum 24 in a plane substantially normal to the scanning plane 42. The other tire of each such pair is in similar rolling contact with edge lip 32 of drum 24. It will be seen that each roller of each such pair preferably rotates in the same plane as the other roller of that pair. This arrangement of roller pairs 92, 94 and 96 in contact with edge lips 30 and 32 serve to constrain lateral motion of the drum normal to the scanning plane 42 relative to the frame 22, but impose no substantial constraint on (1) rotation of the drum within the scanning plane so that scans can be accomplished, or (2) motion of the drum normal to rotation axis 44 so as to accommodate thermal expansion and contraction of the drum.

In a preferred embodiment, drum drive means for driving drum 24 in rotation about axis 44 is provided, typically in the form of DC motor 100. The latter is coupled to drive at least one roller, for example roller 62 as seen in FIGS. 2 and 3, of a pair of rollers on a common axle in at least one of roller trucks 52. Motor 100 can be connected to directly drive roller 70, or alternatively indirectly by a suitable coupling or gear arrangement. Of course other drum drive means may be used. Motor 100 is preferably supported by the truck so that the truck and motor will be free to move relative to the common axis 84, and accommodate torsional twisting of the axis 69 relative to the axis 71, as shown in FIG. 6. It will then be apparent that the remaining rollers in the respective roller trucks 52 are simply follower, idler or free-running driven rollers. Only a single drive motor should prove adequate. For example, because of the low weight of drum 24 and the use of the wheel truck mounting, only a force of 40 to 50 foot-pounds need be applied to rotate the drum adequately, thereby reducing the amount of power required by the prior art tomography systems by a factor of typically about 10.

In operation, annular drum 24 is moved in rotation by the drum drive means provided by wheel 62 by DC motor 100. As drum 24 is rotated, it is supported on trucks 52 such that the resilient tires 90 of the respective wheels minimize the transfer of vibration from frame 22 to drum 24. Note that because of the compliant structure of trucks 52, the multiplicity of rollers in each truck serve to average eccentricities, and imperfections in drum circularity and weight distribution. The weight of drum 24 and its associated components then being supported solely by the averaging trucks, the drum can readily be rotated with an accuracy of within +0.002". The rotation of drum 24 is then stabilized and unaffected by thermal expansion and contraction, and noise is isolated from the drum by the resilient tires, the mounting of noisy components on the frame, and the compliant trucks. Because of the free space provided by the annular interspace 54 and in particular the fact that the space is open around its top half, the drum is free to expand and contract with changes in temperature, and associated elements can be easily removed from frame 22 for servicing and the like with a minimum of effort and down-time.

It should be appreciated that although the preferred embodiment of the invention has been described as a third generation machine, the invention can also be employed in other types of tomography systems, including fourth generation machines. Since certain changes may be made in the above apparatus without departing from the scope of the invention herein involved, it is intended that all matter contained in the above description or shown in the accompanying drawings shall be interpreted in an illustrative and not in a limiting sense.

What is claimed is:

1. In an improved X-ray tomography system comprising a rotatable assembly including an X-ray source for generating X-rays, X-ray detection means for detecting X-rays generated by said source, and support means including frame means for supporting said rotatable assembly for rotation so that said at least X-ray source rotates in a scanning plane, said rotatable assembly including an outer periphery, the improvement wherein said support means further including a plurality of rollers in contact with at least the outer periphery of said rotatable assembly, at least the circular surfaces of said rollers being formed of resilient material for damping transmission of vibration from said frame to said rotatable assembly.

2. The system according to claim 1, wherein the frame means includes an annular frame, and the plurality of rollers are distributed between the frame and the rotatable assembly in rolling contact with the periphery and edges so as to form a cradle for the rotatable assembly.

3. The system according to claim 1, wherein said plurality of rollers includes at least two pairs of rollers for substantially supporting all of the mass of said rotatable assembly for centerless rotation in a rotational plane parallel to or coplanar with said scanning plane; and wherein each said pair of rollers is rotatably mounted on a respective truck means about two rotational axes substantially parallel to the rotation axis of said rotatable assembly, each said truck means being fixed relative to the frame so as to be pivotable about an axis intermediate and parallel to the rotational axes of said each roller of said pair mounted thereon so that each said roller is in such contact with the outer periphery of the rotatable assembly as to rotate with said rotatable assembly as said rotatable assembly rotates relative to said frame means.

4. The system according to claim 3, wherein each of said truck means is formed of compliant material so that the mass of said rotatable assembly is distributed substantially uniformly among said rollers and variations in radial motion of said rotatable assembly are averaged among said rollers.

5. The system according to claim 4, wherein said two pairs of rollers are positioned each on opposite sides of a vertical line passing through said rotation axis so as to support substantially symmetrically said rotatable assembly.

6. The system as defined in claim 4, wherein said plurality comprises a pair of truck assemblies each having mounted thereon two pairs of said wheels arranged in side-by side parallel tandem, each of said truck assemblies being fixed relative to said frame so as to be pivotable about an axis intermediate and parallel to the rotational axes of said each wheel mounted thereon so that each said wheel is in rolling contact with said outer periphery of said rotatable assembly.

7. The system according to claim 1, further including at least three other pairs of rollers, each of said rollers of each said other pair being fixed relative to said frame so as to be in rolling contact with respective opposite sides of said rotatable assembly so as to constrain wobble and out-of-plane transverse motion of said rotatable assembly relative to the rotation plane as the rotatable assembly rotates relative to said frame means.

8. In an improved X-ray tomography system comprising a rotatable assembly including an X-ray source for generating X-rays, X-ray detection means for detecting X-rays generated by said source, and support means including frame means for supporting said rotatable assembly for rotation about an axis of rotation so that at least said X-ray source rotates in a scanning plane about said rotation axis, the improvement wherein:

said support means further includes a plurality of rollers compliantly mounted and fixed relative to said frame means and constructed and arranged for contacting said rotatable assembly such that at any time said rollers contact said rotatable assembly only in a region below said rotation axis so as to rotatably support said rotatable assembly for centerless rotation in plane parallel or coplanar to said scanning plane.

9. The system according to claim 8, wherein the top half of said rotatable assembly is spaced from said frame so as to freely allow for thermal expansion and contraction of said rotatable assembly within said scanning plane.

* * * * *